United States Patent [19]

Gumprecht et al.

[11] Patent Number: 5,302,766

[45] Date of Patent: Apr. 12, 1994

[54] ISOMERIZATION PROCESS

[75] Inventors: William H. Gumprecht, Wilmington, Del.; William J. Steiner, Butler, Pa.; John A. Wehner, Hockessin, Del.

[73] Assignee: E. I. Du Pont de Nemours and Company, Wilmington, Del.

[21] Appl. No.: 70,833

[22] Filed: Jun. 3, 1993

[51] Int. Cl.$^5$ .............................................. C07C 19/08
[52] U.S. Cl. ................................................... 570/151
[58] Field of Search ......................................... 570/151

[56] References Cited

U.S. PATENT DOCUMENTS 4,967,024  10/1990  Gumprecht ..................... 570/168
5,118,887   6/1992  Okazaki ........................... 570/151

Primary Examiner—Alan Siegel
Attorney, Agent, or Firm—Herbert M. Wolfson

[57] ABSTRACT

A process for converting the isomers of HCFC-123 to HCFC-123 using $TaF_5$ and/or $Nb_5$ in the absence of HF.

6 Claims, No Drawings

ISOMERIZATION PROCESS

FIELD OF THE INVENTION

This invention relates to a process for isomerizing $CClF_2CHClF$ (HCFC-123a) and $CCl_2FCHF_2$ (HCFC-123b) to $CF_3CHCl_2$ (HCFC-123); and, more particularly, to a process performed in the absence of hydrogen fluoride.

BACKGROUND OF THE INVENTION

Closed-cell polyurethane foams are widely used for insulation purposes in building construction and in the manufacture of energy efficient electrical appliances. To prepare these foams, expansion or blowing agents are required. Historically, trichlorofluoromethane (CFC-11) has been the choice blowing agent for these foams as well as for the polyurethane/polyisocyanurate foams. CFC-11, along with 1,1,2-trichloro-1,2,2-trifluoroethane (CFC-113), has been the blowing agent of choice in the preparation of phenolic foams.

However, in Sept. 1987, when the United Nations, through its Environmental Program Unit, issued a proposal calling for the reduction in world-wide production of fully halogenated chlorofluorocarbons such as CFC-11 and CFC-113 (ratified on Jan. 1, 1989), there began a search for an acceptable substitute for CFC-11. That is, there was an urgent need for an effective blowing composition that would contribute little or, preferably, nothing to the stratospheric ozone depletion process nor to the global warming process known as the "greenhouse effect".

HCFC-123, which is a hydrogen-containing and, therefore, a "not fully" halogenated chlorofluorocarbon, has now become the choice substitute for CFC-11 in blowing compositions. However, the blowing agent market demands that the HCFC-123 contain less than 1% of any isomeric impurities such as HCFC-123a and HCFC-123b. It had been found that these impurities, particularly HCFC-123a, have objectionable reactivity toward the other components in the blowing formulations.

Removing the objectionable isomeric dichlorotrifluoroethanes is extremely difficult. The isomers are too close boiling for economic separation by conventional methods.

DESCRIPTION OF PRIOR ART

Japanese Patent Application JO 1,258,630 discloses that HCFC-123a and HCFC-123b are isomerized to $CF_3CHCl_2$ by selected aluminum chlorofluorides and oxychlorofluorides or catalysts. Similarly, Japanese Patent JO 2,040,332 discloses that hydrogen-containing chlorofluorohydrocarbons can be isomerized using catalysts containing aluminum, fluorine, chlorine and oxygen. Neither reference, however, suggests the use of an isomerizing agent other than an aluminum chlorofluoride or aluminum oxyfluoride.

European Patent Application 317,981 discloses preparation of $CF_3CCl_2F$ (CFC-114) by (1) catalytically isomerizing $CClF_2CCl_2F$ (CFC-113) to $CF_3CCl_3$(CFC-113a) in the presence of a halide or oxide of Al, Cr, Mg, Ca, Sr, Fe, Ni or Co, followed by catalytically fluorinating the isomerization product in the presence of a halide or oxide of one of the above metals or of Sb, Ta or Nb. It will be noted that Nb and Ta are disclosed as catalysts for fluorination, not for isomerization. Also, there is no disclosure relating to the isomerization of hydrogen-containing chlorofluorocarbons such as $CClF_2CHClF$ or $CCl_2FCHF_2$.

In U.S. Pat. No. 4,967,024, issued Oct. 30, 1990, the patentees had found that, in the production of HCFC-123 from certain specified halogenated alkenes and alkanes, i.e., $CCl_2=CCl_2$ and $CCl_3CHCl_2$, in a liquid-phase process using at least the stoichiometric amount of hydrogen fluoride along with a $TaF_5$ or $NbF_5$ catalyst, isomers of HCFC-123 are formed in relatively high and objectionable amounts, particularly large amounts of HCFC-123a. They also found that the isomer content of the reaction product can be substantially reduced (to as low as non-detectable levels) when the products remain in contact with the reaction mass for a time sufficient to accomplish the desired low isomer result. The residence time sufficient to accomplish this was dependent upon the HF and the starting material feed rates, the reaction temperature and pressure and the temperature of the gas leaving the reactor.

It is an object of this invention to isomerize $CClF_2CHClF$ and/or $CCl_2FCHF_2$ to $CF_3CHCl_2$ without using any of the highly corrosive and toxic hydrogen fluoride. It is a further object to produce $CF_3CHCl_2$ substantially free of the more highly fluorinated products as well as free from the aforementioned isomers.

SUMMARY OF THE INVENTION

The objects are accomplished by a process in which at least one of HCFC-123a and HCFC-123b is agitated with at least 0.1 mole, preferably 0.5 to 2 moles, per mole of isomer of at least one of tantalum pentafluoride ($TaF_5$) and niobium pentafluoride ($NbF_5$), preferably $TaF_5$, for about 1 to 20 hours at a temperature of about 100° C. to 200° C., preferably 150° C. to 185° C., to produce a composition containing at least 90% by weight of HCFC-123.

DETAILED DESCRIPTION OF THE INVENTION

The isomerization is generally conducted under anhydrous conditions. The reactants are introduced with or without $CF_3CHCl_2$ or an inert diluent, in any order, into a suitable reaction vessel, are agitated and raised to an appropriate temperature and held at a pressure and for a time sufficient for the isomerization to proceed to the desired extent, which is preferably to an isomer content below about 10%, more preferably to below 5%.

"Complete" conversion of HCFC-123a to HCFC-123 is not possible since there is a small equilibrium content of HCFC-123a which remains. At 140° C., the equilibrium content is approximately 80 ppm HCFC-123a. Raising the temperature somewhat causes the equilibrium HCFC-123a content to increase, i.e., to 0.16% HCFC-123a at 315° C.

The temperature for isomerization is preferably in the range of from about 100° to 200° C., more preferably 150° to 185° C. Below about 100° C., the reaction tends to be too slow to be useful; above about 200° C. the yield of $CF_3CHCl_2$ may be reduced by side reactions.

Pressure is not very critical but should be sufficient to maintain the isomer(s) to be converted in effective contact with the metal pentafluoride, i.e., in the liquid state. The metal pentafluoride catalyst can be neat (molten) or it can be dissolved or dispersed in an inert liquid diluent. $CF_3CHCl_2$ is a suitable diluent, particularly in the absence of HF, since the metal pentafluorides are miscible with $CF_3CHCl_2$. The pressure may vary widely from atmospheric to super-atmospheric, preferably the latter. Autogenous pressures are convenient and, therefore, preferred.

The catalyst, which may be $TaF_5$ or $NbF_5$ or a mixture thereof, is employed in effective isomerizing amount, which normally correspond to at least 0.1 mole per mole of the isomer content and preferably about 0.5 to 2 mole per mole of isomer. Greater excesses of the catalyst provide no added benefit. $TaF_5$ is preferred for its greater activity. The reaction time can vary from about 1 to 20 hours depending on the metal fluoride and its concentration, the temperature and the result desired.

Thus, it is clear that the metal pentafluorides, without added HF as in the prior art, although possibly requiring higher reaction temperatures and/or longer reaction times, provide significant advantages over the metal pentafluoride/HF combination. The metal pentafluorides are miscible with the dichlorotrifluoroethanes, generate lower internal pressures, are less corrosive to ordinary materials of construction, produce fewer side products, and, using them alone, eliminates HF, an extremely hazardous/toxic substance.

Water should be excluded as much as possible from the reaction zone. The isomeric materials and the pentafluorides are normally water free and may be used as such directly. Moisture can be excluded from the reaction vessel by use of appropriate moisture traps or other means employed in the art. The pentafluoride may be re-used one or more times to isomerize additional isomer charges provided the reaction mass is maintained anhydrous during the recovery of $CF_3CHCl_2$ therefrom.

The isomerization product can be isolated by any of a variety of well known techniques. Distillation from the pentafluoride, drowning on ice, washing with aqueous caustic followed by washing with water and drying with molecular sieves are representative techniques. Another isolation procedure involves washing the organic fraction with 20.7% aqueous HCl pre-cooled to −60° C. This permits collection of material boiling below ice temperature. The scrubbed products can be further purified by fractional distillation. The organic fraction is preferably separated from the pentafluoride anhydrously, as by distillation, and the residual pentafluoride is re-usable to isomerize additional isomer charges.

The reaction vessel is constructed from material resistant to the reactants. Examples include stainless steels, high nickel alloys such as monel, "Hastelloy" and "Inconel", and plastics such as polychlorotrifluoroethylene and polytetrafluoroethylene. Of the metallics, stainless steels are preferred.

THE EXAMPLES OF THE INVENTION

The following examples were carried out in a 600 ml Hastelloy C-276 reactor. $CClF_2CHClF$ (HCFC-123a) was measured by gas chromatographic analysis and showed one peak at 11.70 sec. covering 99.99% of the area and another at 17.32 sec. with 0.005% of the area. The 11.70 sec. peak, attributed to HCFC-123a, probably included about 3% HCFC-123b and a very minor amount of HCFC-123.

EXAMPLE 1

107 Grams (0.39 mole) of $TaF_5$ and 400 grams of HCFC-123a (2.61 moles) were added to the autoclave in a drybox. The reactor was sealed and heated to 130° C. while being agitated at 500 rpm. The pressure reached 185 psig. Reaction product samples were taken periodically, as noted below, and analyzed gas-chromatographically and mass-spectrographically with the following results:

| Sample No. | Time Hours | Composition (Area %) | | |
|---|---|---|---|---|
| | | HCFC-123a | HCFC-123b | HCFC-123 |
| 1 | 21 | 66.59 | 2.50 | 30.74 |
| 2 | 42 | 46.37 | 2.31 | 50.98 |
| 3 | 114 | 6.42 | 1.97 | 91.37 |

No halogen exchange products were detected.

EXAMPLE 2

The volatile materials remaining in the reactor following Example 1 were vented by opening the reactor valve and heating it to 180° C. for about 0.5 hour. 45.7 Grams (0.30 mole) of HCFC-123a was added (corresponding to a $TaF_5$/HCFC-123a mole ratio of 1.3 based on the $TaF_5$ charge used in Example 1). The reactor was sealed and heated under agitation to 150° C., the autogenous pressure reaching 150 psig. Samples were taken and analyzed as before with the following results:

| Sample No. | Time Hours | Composition (Area %) | | |
|---|---|---|---|---|
| | | HCFC-123a | HCFC-123b | HCFC-123 |
| 1 | 1 | 78.99 | 2.53 | 16.96 |
| 2 | 2 | 29.46 | 1.64 | 63.22 |
| 3 | 3 | 7.26 | 1.37 | 90.17 |
| 4 | 4 | 6.17 | 1.27 | 90.88 |
| 5 | 5 | 0.62 | 0.62 | 97.29 |

EXAMPLE 3

The procedure of Example 1 was repeated except that $NbF_5$ (49.2 grams, 0.26 mole) and HCFC-123a (31 grams, 0.20 mole) were used, and the reaction temperature was 150° C. at a pressure of 150 psig. The results are tabulated below:

| Sample No. | Time Hours | Composition (Area %) | | |
|---|---|---|---|---|
| | | HCFC-123a | HCFC-123b | HCFC-123 |
| 1 | 3.75 | 56.56 | 1.55 | 37.82 |
| 2 | 6.75 | 33.11 | 0.80 | 62.89 |
| 3 | 11.75 | 3.12 | 0.05 | 94.66 |

What is claimed is:

1. A process for converting at least one of the isomers, $CCl_2FCHF_2$ and $CClF_2CHClF$ to $CF_3CHCl_2$ comprising
   (a) forming a reaction mixture consisting essentially of at least one of the isomers, $CClF_2CHClF$ and $CCl_2FCHF_2$, and an effective amount of at least one of $TaF_5$ and $NbF_5$ without the addition of HF;
   (b) maintaining said reaction mixture at a temperature and pressure and for a time effective to result in a decrease in the isomer content and an increase in the $CF_3CHCl_2$ content; and (c) recovering a dichlorotrifluoroethane composition from the reaction mass enriched in $CF_3CHCl_2$.

2. The process of claim 1 wherein the metal pentafluoride is $TaF_5$.

3. The process of claim 2 wherein the amount of $TaF_5$ corresponds to about 0.1 mole-2 moles per mole of isomer.

4. The process of claim 1 wherein the temperature is in the range of from about 100° to about 200° C. and the pressure is autogenous.

5. The process of claim 1 wherein the temperature is in the range of from about 150° C. to 185° C.

6. The process of claim 1 wherein the reaction mixture is maintained at said temperature and pressure until the isomer content of the reaction product is less than about 1.0 mole percent of the product.

* * * * *